United States Patent [19]

Baart de la Faille

[11] Patent Number: 5,119,826
[45] Date of Patent: Jun. 9, 1992

[54] METHOD AND APPARATUS FOR SCREENING THE HEARING OF A YOUNG CHILD

[75] Inventor: Leonard M. B. Baart de la Faille, Naarden, Netherlands

[73] Assignee: Nederlandse Stichting Voor Het Dove en Slechthorende Kind, Amsterdam, Netherlands

[21] Appl. No.: 560,576

[22] Filed: Jul. 31, 1990

[30] Foreign Application Priority Data

Aug. 1, 1989 [NL] Netherlands ............... 8901985

[51] Int. Cl.$^5$ .............................. A61B 5/00
[52] U.S. Cl. ................................. 128/746; 73/585
[58] Field of Search .......................... 128/746; 73/585

[56] References Cited

U.S. PATENT DOCUMENTS

| | | | |
|---|---|---|---|
| 3,906,158 | 9/1975 | Lake | 73/585 |
| 3,938,500 | 2/1976 | Simmons | 128/746 |
| 4,139,730 | 2/1979 | Franklin | 73/585 |
| 4,489,610 | 12/1984 | Slavin | 128/746 |
| 4,862,505 | 8/1989 | Keith et al. | 73/585 |

FOREIGN PATENT DOCUMENTS

| | | |
|---|---|---|
| 2262352 | 7/1973 | Fed. Rep. of Germany. |
| WO85/00509 | 2/1985 | World Int. Prop. O. . |

OTHER PUBLICATIONS

"Researchers Refine Technique to Test Hearing in Sleeping Newborns", *N.T.I.S. Tech Notes*, No. 1E, Jan. 1985, pp. 27-28.

*Primary Examiner*—Max Hindenburg
*Attorney, Agent, or Firm*—Young & Thompson

[57] ABSTRACT

A method and apparatus for screening the hearing of a young child are disclosed. The method comprises providing, outside the field of view, a series of natural sound stimuli, which are controlled in intensity and spectrum, in various frequency bands and recording, within a time interval after each stimulus, the assessment, given by a researcher, of the response of the child, and testing the response on the basis of pass/fail criteria. The intensity and spectrum of the subsequent sound stimuli in the same or in another frequency band are determined on the basis of the result of each response test. The sound stimuli mentioned are based on processed sound signals derived from the environment. The sound stimuli are presented according to an adaptive protocol program, each response test codetermining the course of the screening. The apparatus includes at least one loudspeaker for emitting the sound stimuli and a processing and control unit. The processing and control unit comprises a digital memory for storing the sound stimuli in a number of frequency bands, a stimulus response unit, and a screening pattern processor employing an adaptive protocol program.

13 Claims, 3 Drawing Sheets

A. CONDITIONING + POSSIBLE REPEAT

B. FOUR STIMULI (35 dB)

C. NO OR ONE GOOD
   RESPONSE: / FOUR STIMULI (40 dB)

D. FOUR STIMULI (35 dB)

E. REPEAT SERIES (35/40 dB)
   —SELF-REGULATING
   —PASS/FAIL CHECK
      TOTAL NUMBER OF STIMULI ≤ 16

METHOD AND APPARATUS FOR SCREENING THE HEARING OF A YOUNG CHILD

FIELD OF THE INVENTION

The invention relates to a method and apparatus for screening the hearing of a young child.

BACKGROUND OF THE INVENTION

It is known in practice to screen the hearing of very young children with the aid of sound stimuli. In this method, the responses of these babies can be assessed by a researcher.

This known method has in practice considerable drawbacks. In general, for the apparatuses used in the method at least two researchers are necessary, viz. one researcher to present the sound stimuli outside the field of view of the child and another to record the response and to determine the course of the test on the basis of instructions. The sound stimuli emitted by the known apparatus provide inadequate facilities for testing different frequencies. The said stimuli can also be varied by the apparatus mentioned only to a limited extent, as a result of which the reliability of the responses is very dependent thereon. To evaluate the tests well and to monitor the quality associated with it, a time-consuming and laborious administrative process is necessary.

OBJECT OF THE INVENTION

The object of the invention is to deal with this and to provide a method and apparatus for testing the hearing of very young children which also makes it possible to increase the validity of the test very considerably.

SUMMARY OF THE INVENTION

This is achieved in a method of the type mentioned in the preamble by providing, outside the field of view, a series of natural sound stimuli, which are controlled in intensity and spectrum, in various frequency bands and recording, within a time interval after each stimulus, the assessment, given by a researcher, of the response of the child, and testing the response on the basis of pass/fail criteria. Specifically, this method is used for testing the hearing of children from six to thirty months.

The apparatus for carrying out the above-mentioned method, which is provided with at least one loudspeaker for emitting the sound stimuli and a processing and control unit, is further characterized in that said processing and control unit comprises a digital memory for storing the sound stimuli in a number of frequency bands, a stimulus response unit, and a screening course processor employing an adaptive protocol program.

The above-mentioned method and apparatus according to the invention can be used to emit sound stimuli, which are controlled in intensity and spectrum, in various frequency bands and can test the responses of the babies under examination by a researcher on the basis of response assessment criteria. The results of said responses, which are recorded by the researcher in the apparatus, determine the subsequent pattern of the screening test, which is controlled by a microprocessor with the aid of the protocol program mentioned.

DESCRIPTION OF THE RELATED ART

From U.S. Pat. Nos. 3,808,811 and 4,284,847, it is known per se to use automated tests of the hearing. In these cases, however, it is not a method involving sound stimuli derived from the natural environment which is used, but an automated threshold approach method which is known per se. Specifically, this is not adapted for testing the hearing of very young children. French Patent Specification 7,619,023 discloses a method and apparatus for testing the hearing of young children, but only at 2 years of age, specialist personnel being necessary. In general, it may be stated that automated hearing threshold determinations are known. In these, the hearing threshold is determined for each test frequency with the aid of a so-called up-down routine in which the threshold is approached in steps as closely as possible.

It is known from U.S. Pat. No. 4,139,730 to use band-filtered speech signals. These filter bands have to be narrow enough for it to be possible to test the hearing function for individual frequencies. Such narrow-band speech signals, however, lose the natural character to a very significant degree and are usually no longer recognized as speech. This means that the objective, viz. the use of "speech-pattern stimuli", is not achieved. The consequence thereof is that there is a great risk that many children do not react adequately to said stimuli and the effectiveness of the stimulus is lost.

German Patent Specification 2,262,352 discloses the use of a tone sliding over a wide frequency spectrum. This cannot produce frequency-specific information about the hearing function. Serious hearing losses (for example treble loss) in children would reduce the stimulus to "warble" tones as a result of using a narrow-band sliding tone. The effectiveness of this is limited in the case of children.

BRIEF DESCRIPTION OF THE DRAWINGS

The invention will be illustrated in more detail by reference to the accompanying figures, in which.

DESCRIPTION OF THE PREFERRED EMBODIMENTS

Figure 1:
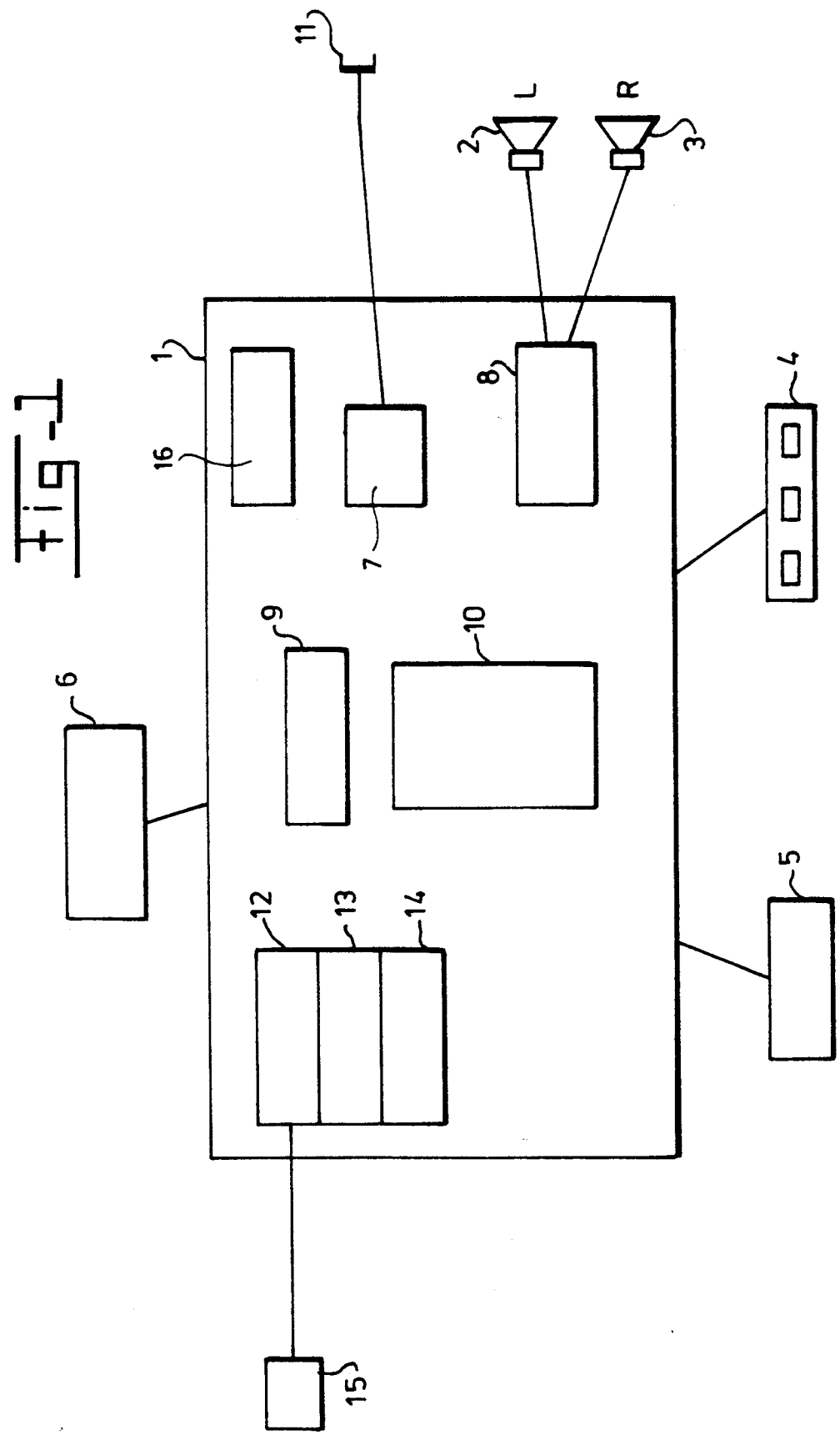
FIG. 1 shows, very generally, a block diagram of the apparatus according to the invention.

The apparatus shown in FIG. 1 for screening the hearing of a young child comprises at least one processing and control unit 1 having two loudspeakers 2, 3 for reproducing sound stimuli generated by the (8 bit, 20 kHz) audio interface 8; a stimulus-response unit 4 having three buttons with which the researcher can initiate a stimulus or the timing thereof (one button) and can record or feed in the response of the young child (one button for the right ear and one button for the left one); a keyboard 5 and a display screen 6 (for example LCD), which combination provides the researcher with the facility to feed in personal data about the baby, to select a test protocol, and to clarify the course of the screening test; a central processing and control device 10, for example a microprocessor; and a working memory 9 for storing the test protocols, the sound stimuli to be generated and the test results. These data stored in the memory can be altered remotely as such via a telephone line. The apparatus further comprises an integrated modem 7 for communication with a regional computer via a standard telephone plug 11 of the telephone network. The apparatus also comprises some analog circuits 12, 13, 14 for converting digital sound information originating from an external source or background memory 15 to audible sound stimuli within accurately specified limits.

The processor also contains a program for reading the sound stimuli stored in a development system into the memory of the screener.

Of great importance in the present invention is the fact that sound stimuli are generated which are standardized from an audiological viewpoint and which are synthesized on the basis of environmental sounds. Thus, for example, a rattle, a domestic animal or other sound stimuli based on sounds which arouse babies' interest can be generated with varying intensity and frequency. These natural sound signals have the advantage that, like speech, they have a low response threshold for the young child. It is essential that they are selected and filtered in a manner such that the natural character is retained while a sufficiently narrow-band stimulus is nevertheless obtained. These analog sounds are digitalized in the development system, processed further and finally stored in a memory with the amplitude being limited without distortion products outside the stimulus frequency band.

The amplitude limitation is necessary because children having a sensory neural hearing loss are often oversensitive to signal peaks (recruitment phenomenon). With constant peak level, the mean signal level can be increased as a consequence of the amplitude limitation. This produces an effective sound stimulus.

In contrast to the determination of the hearing threshold used in the known method employing discrete frequency tones, a response pattern is now determined, with the aid of an algorithm from the test protocol, for a large number of different sound stimuli whose frequency spectra are distributed over various frequency bands. In contrast to the known technique, the algorithm mentioned does not work through the various test frequencies consecutively but alters all the test frequency bands continuously. Various stimuli can be included for each frequency band, as a result of which a large variation can be achieved in said sound stimuli. The various frequency bands can be used interspersed with one another as determined with the aid of the test protocols. The test protocol processor is also able to offer the various frequency bands both to the right ear and to the left ear via two loudspeakers. In this connection, the protocol program is also able to activate a response energizing circuit 16 so that a good response, i.e. a response assessed according to the assessment rules, is confirmed or conditioned by, for example, light signals. This can be done, for example, with a small lamp which is fitted on each loudspeaker and is able to flash.

Furthermore, a separate program provides the test protocol which determines the screening course or pattern. The protocol processor used for this automatically caters for adequate alternation of the stimulated left and/or right ear. The researcher is able to determine the instant of emission of the stimulus by means of a stimulus key or button on the unit 4. By depressing the one response button or the other, he is also able to cause a good response of the one ear or the other ear of the child to be recorded. In order to limit an incorrect assessment of the response by the researcher, a time window in which the response assessment must occur is created subsequent to the sound stimulus previously emitted. Every response pattern can be tested after each stimulus against pass/fail criteria.

According to the invention, the algorithm will then determine the further selection of intensity and spectrum of the subsequent sound stimuli on the basis of the response pattern. This makes it possible to allow for varying reaction patterns of the young children. It has been found important in this connection that the reactions of babies to sound stimuli are very dependent on many factors such as varying attention, nature of the stimuli, background noise, the way in which the test is carried out, etc. Such strongly varying reactions of these young children differ considerably from the responses such as those which are given in the currently known techniques via a pushbutton which is operated by the person concerned, an older child or an adult.

Present apparatus can advantageously be used for the purpose of testing hearing in a diagnostic environment, it being possible to select frequency band and intensity of the stimulus and also the left or right loudspeaker with the aid of the keyboard and to retain the responses in an audiogram on the viewing screen. It is therefore also possible to condition the response visually by means of, for example, light signals from an energizing device.

In addition, with the method and apparatus according to the invention it is possible to make a continuous statistical assessment by means of the protocol, with the result that the screening time needed can be optimized and the level of reliability of the reaction threshold found can be influenced.

A great advantage is that the abovementioned apparatus can be linked via modem and telephone lines to a central, for example, a regionally installed, computer which makes it possible to coordinate and administratively guide a screening program centrally for a large population of young children. In this connection, a uniform screening can be used for all the children, with the test evaluation automated centrally, and the screening protocols defined and adjusted centrally.

Figure 2:
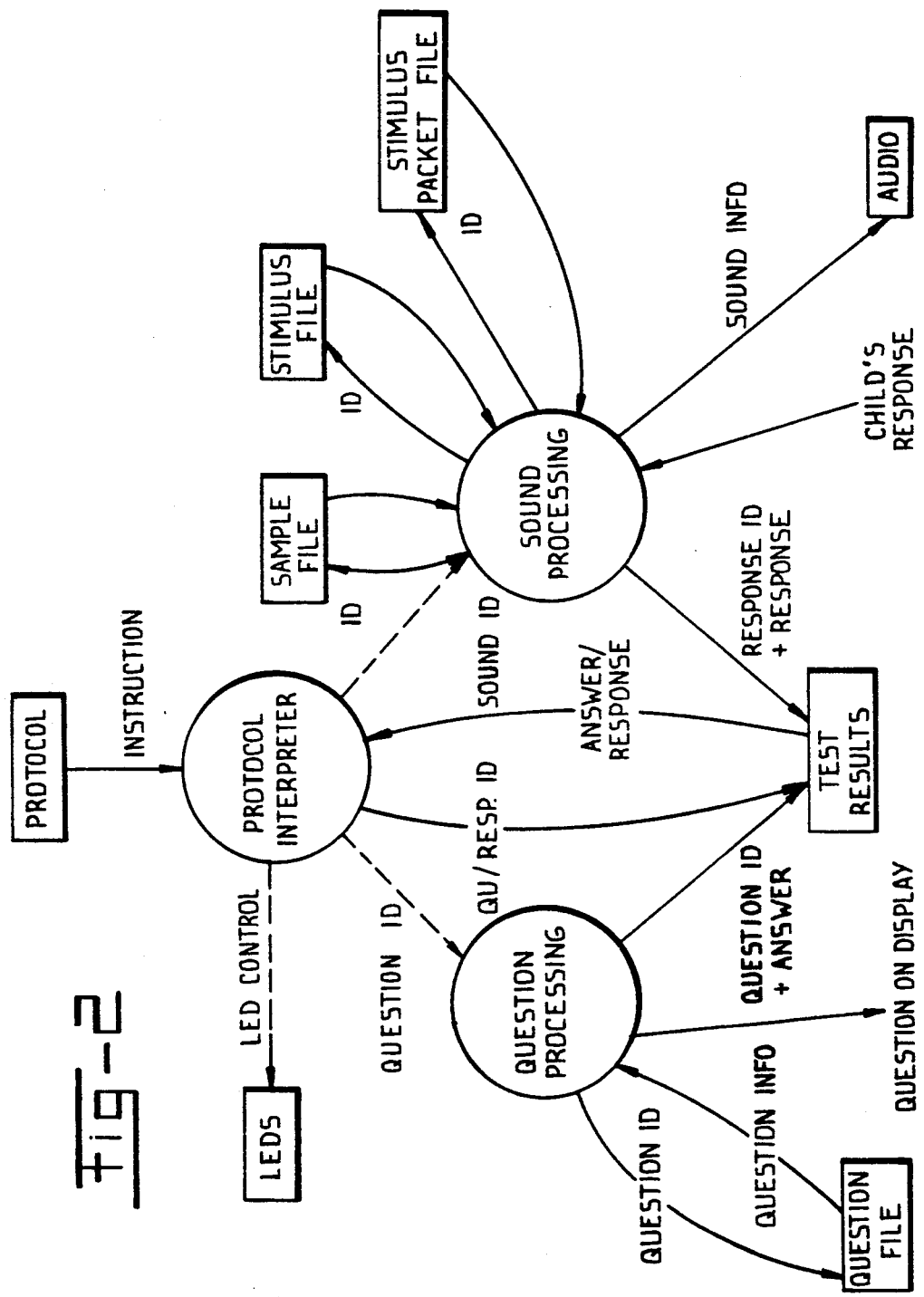
FIG. 2 gives an example of a data flow diagram of the protocol processing in the method according to the invention.

The data flow diagram shown in FIG. 2 is an example of the protocol processing of the screening apparatus. In this, → indicates the data flow and      indicates the control or monitoring.

The screening apparatus is "loaded" with a protocol program which can be processed by the protocol interpreter (PI). The PI has access to the various files:

Sample file: digital representation of a "basic sound", for example a single tap on a tuning fork, a bird "whistle", a cat miaow, etc.

Stimulus file: this comprises parameter data with which a stimulus can be defined with the aid of basic sounds from the sample file. A basic sound may, for example, be repeated with variable pause intervals and intensity.

Stimulus packet file: this makes it possible to define series of stimuli with, for example, decreasing intensity.

Question file: this makes it possible to define (administratively, in content) questions (for example multiple choice, open question etc).

Test results file: detailed test results, response times and answers.

The PI runs through the protocol program and in doing so generates the diverse sound stimuli and questions on the display, and records responses and answers in a file. The course of the protocol program is influenced by the responses. The PI also regulates the alternating left-right stimulation, the response conditioning by means of "LEDs" and the time window for the response.

Figure 3:
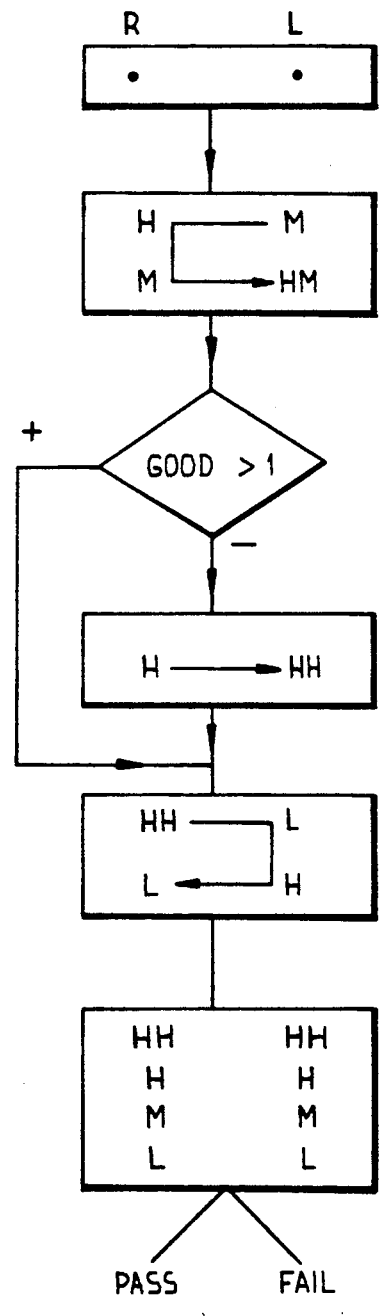
FIG. 3 gives a diagrammatic example of a protocol program with subsequent stimuli.

FIG. 3 gives, diagrammatically, an example of a possible test protocol. In this protocol, three separate frequency bands are tested against a pass/fail criterion. Said pass/fail criterion can be adapted to the objective of the screening, for example:

a good response, i.e. a "pass", must be recorded in all the frequency bands and for both ears with a sound intensity of 35 dB, a "fail" being recorded in the converse case; and in addition, a second good response must be recorded for the high frequency band at 35 or 40 dB.

The frequency bands and the pass/fail criterion are shown in Table I.

TABLE I

| | Frequency band (Hz) | Level (dB) | |
|---|---|---|---|
| | | pass I | pass II |
| L | 150–1000 | 35 | 35 |
| M | 1500–3000 | 35 | 35 |
| H | 3500–6000 | 35 | 40 |
| HH | 3500–6000 | 40 | 35 |

A response is indicated by the researcher with the aid of two response keys (L, R) if there is a prompt turning movement through 90° or if a clear localization occurs of one of the two loudspeakers which are set up at an angle on either side behind the child. The protocol program records this as a good response if the response occurs during the sound stimulus (not more than 5 sec) or within the response window after the sound stimulus (0.5). If the child turns its head to the correct side, after the key concerned is depressed, a good response is conditioned by means of small red lamps in the speakers which flash for 0.5 sec, after which the sound stimulus is discontinued.

A: At the beginning of the test, the child is conditioned by means of a slowly swelling sound stimulus (to 70 dB). If this is not followed by a response on one or both sides, the conditioning is repeated with another stimulus.

B: Four stimuli are then presented in sequence at a level of 35 dB. The sequence is indicated by the arrow.

C: If no response or only one good response is recorded, presentation of two stimuli at 40 dB follows.

D: Four stimuli at 35 dB are then presented.

E: After this series, in which all the frequency bands have been presented, there follow repeats in a second, third or, if necessary, fourth run for the stimuli with an unsatisfactory response.

During the repeat series, the protocol program caters for:
- alternation of the sound stimuli,
- alternating left-right stimulation (a maximum of two consective stimuli at one side),
- adjustment of the level for H and HH stimuli,
- discontinuation of the test if the pass criterion can no longer be reached,
- discontinuation of the test as soon as the pass criterion is reached,
- discontinuation of the test after a maximum of sixteen sound stimuli.

I claim:

1. Apparatus for screening the hearing of a young child comprising: at least one loudspeaker for emitting sound stimuli and a processing and control unit including a digital memory for storing the sound stimuli in a number of frequency bands, a stimulus response unit, and a screening pattern processor employing an adaptive protocol program.

2. Apparatus according to claim 1, further comprising a keyboard and display screen connected to the processing and control unit, a printer and/or telephone modem and/or computer interface via which data and detailed test results of a number of children can be registered and exchanged.

3. Apparatus according to claim 1, wherein the natural sound stimuli are stored in the memory with digital amplitude limitation without distortion products outside the stimulus frequency band.

4. Apparatus according to claim 1, wherein the processing and control unit further includes an energizing device for emitting a signal after each correct response.

5. Method for screening the hearing of a young child which comprises providing, outside the field of view, a series of natural sound stimuli, which are based on processed sound signals derived from the environment, such that each sound stimulus to be emitted in a frequency band is a composite natural sound signal, and which are controlled in intensity and spectrum in various frequency bands, determining, within a time interval after each stimulus, an assessment, given by a researcher, of the response of the child, testing the response on the basis of pass/fail criteria, and determining, on the basis of the result of each response test in accordance with an adaptive protocol program, the intensity and spectrum of the subsequent sound stimuli in the same or in following frequency bands.

6. Method according to claim 5, where said frequency bands comprise bands of approximately 150–1000 Hz, approximately 1500–3000 Hz and approximately 3500–6000 Hz.

7. Method according to claim 5, wherein a separate pass/fail criterion is established for each frequency band.

8. Method according to claim 7, wherein said pass/fail criterion represents an intensity in dB of a sound stimulus presented to the young child.

9. Method according to claim 8, wherein said pass/fail criterion for said three frequency bands is 35 dB for a first run.

10. Method according to claim 5, wherein prior to presenting the series of natural sound a conditioning stimulus with a gradually increasing intensity, is presented.

11. Method according to claim 5, wherein the series of sound stimuli are emitted in said frequency bands via a left and/or right loudspeaker.

12. Method according to claim 5, wherein each correct response is visually conditioned by means of a light signal.

13. Apparatus according to claim 4, wherein the energizing device includes means for emitting a light signal after each correct response.

* * * * *